(12) United States Patent
Roecker et al.

(10) Patent No.: US 7,885,771 B2
(45) Date of Patent: Feb. 8, 2011

(54) DEVICE AND METHOD FOR THE DETECTION AND EVALUATION OF EXPIROGRAMS

(75) Inventors: Kai Roecker, Freiburg (DE); Stephan Prettin, Freiburg (DE)

(73) Assignee: Universitaetslinkum Freiburg, Freiburg (DE)

( * ) Notice: Subject to any disclaimer, the term of this patent is extended or adjusted under 35 U.S.C. 154(b) by 649 days.

(21) Appl. No.: 11/573,631

(22) PCT Filed: Aug. 11, 2005

(86) PCT No.: PCT/EP2005/008768

§ 371 (c)(1),
(2), (4) Date: Aug. 17, 2007

(87) PCT Pub. No.: WO2006/018237

PCT Pub. Date: Feb. 23, 2006

(65) Prior Publication Data

US 2008/0114551 A1 May 15, 2008

(30) Foreign Application Priority Data

Aug. 12, 2004 (DE) .................. 10 2004 039 194

(51) Int. Cl.
*G01N 33/50* (2006.01)

(52) U.S. Cl. ......................... 702/24; 600/526

(58) Field of Classification Search .................. 702/24, 702/30, 50, 182–185; 600/526
See application file for complete search history.

(56) References Cited

U.S. PATENT DOCUMENTS 5,971,934 A * 10/1999 Scherer et al. .............. 600/526
6,251,082 B1 6/2001 Rayburn

OTHER PUBLICATIONS

A.H. Kars et al.; "Dead space and slope indices from the expiratory carbon dioxide tension-volume curve"; The European Respiratory Journal; Official Journal of the European Society for Clinical Respiratory Physiology; Bd. 10, Nr. 8; pp. 1829-1836; Aug. 1997.

(Continued)

*Primary Examiner*—Edward Raymond
(74) *Attorney, Agent, or Firm*—Fish & Richardson P.C.

(57) ABSTRACT

The invention relates to an apparatus for the acquisition and interpretation of expirograms comprising:

a gas measuring probe that is designed to determine the gas concentration $f_{mess}$ of a gas in exhaled respiratory air;

a reading device that is connected to the gas measuring probe via signal and is designed to read for a plurality of values $x_1, \ldots, x_N$ of an exhaled volume of the exhaled respiratory air the respective determined gas concentrations $f_{mess}(x_1), \ldots, f_{mess}(x_N)$ from the gas measuring probe;

a storage device that is designed to store the values $x_1, \ldots, x_N$ assigned to the gas concentrations $f_{mess}(x_1), \ldots, f_{mess}(x_N)$;

a function fitting unit that is connected to the storage device via signal and that is designed to determine a non-linear fit function $$f(x) = g(x) \cdot h(x) + \text{Offset}_{Gas}$$

for the stored gas concentrations $f_{mess}(x_1), \ldots, f_{mess}(x_N)$ by determining functions $g(x)$ and $h(x)$ wherein $h(x) = a + b \cdot x$ $g(x)$ is a continuously differentiable, non-linear function with $$g(0) = 0 \text{ and } \lim_{x \to \infty} g(x) = const,$$

a, b and const being constants and $\text{Offset}_{Gas}$ being a constant, mean concentration of the gas in room air.

22 Claims, 9 Drawing Sheets

OTHER PUBLICATIONS

G. R. Neufeld et al; "Modelling steady state pulmonary elimination of He, SF6 and CO2: Effect of morphometry"; Respiration Physiology; Bd. 88, Nr. 3; pp. 257-275; Jun. 1992.

Johnnie W. Huang et al; "Airway cross section strongly influences alveolar plateau slope of capnograms for smaller tidal volumes"; Respiration Physiology; Bd. 119, Nr. 1; pp. 51-55; Jan. 2000.

Golo von Basum et al; "Online recording of ethane traces in human breath via infrared laser spectroscopy"; Journal of Applied Physiology; Bd. 95, Nr. 6; pp. 2583-2590 Dec. 2003.

Ward S. Fowler; "Lung Function Studies, II The Respiratory Dead Space"; American Physiological Society; vol. 154; Mar. 16, 1948.

PCT International Search Report and Written Opinion in International Application No. PCT/EP2005/008768; 13 pages; Jan. 31. 2006.

International Preliminary Report on Patentability, mailed Feb. 20, 2007, 7 pages.

* cited by examiner

16

(a)

(b)

(c)

(d)

(e)

(a)

(b)

(c)

(a)            (b)            (c)

DEVICE AND METHOD FOR THE DETECTION AND EVALUATION OF EXPIROGRAMS

CROSS-REFERENCE TO RELATED APPLICATIONS

This application is a filing under 35 U.S.C. §371 and claims priority to international patent application number PCT/EP2005/008768 filed Aug. 11, 2005, published on Feb. 23, 2006, which claims priority to patent application number 10 2004 039 194.7 filed in Germany on Aug. 12, 2004.

The invention relates to an apparatus for the acquisition and interpretation of expirograms, a method for the acquisition and interpretation of expirograms as well as a respective computer program product.

Shape features of so-called expirograms are of special interest for scientific and diagnostic purposes. An expirogram is the characteristic course of the gas concentration of the respiratory gases carbon dioxide ($CO_2$) and oxygen ($O_2$) as a function of tidal volume or time, respectively. For example, carbon dioxide is removed from the body with each expiration and oxygen from the air is introduced into the cardiovascular system. In the course of every expiration and based on the exhaled tidal, a characteristic course of the gas concentration of these two respiratory gases is obtained.

In mammals and humans, air is introduced through the trachea via the mouth or the nose. The larynx can close off the trachea against the pharynx, e.g. during swallowing. The trachea bifurcates into the primary bronchials that lead into the lungs. There, the primary bronchials split into even thinner bronchials that, via so-called bronchioles, end in the alveolar channels and finally in small vesicles, the alveoli. This means the respiratory epithelia are vented by way of a bi-directional alternating steam (inhaling and expiration).

Of special importance in this context is the so-called "dead space" of a lung. Dead space is the volume of the lung that does exchange air but does not partake in the gas exchange with the body tissue. In healthy people dead space above all includes the transport path of respiratory air such as the trachea and tracheal branches (bronchial).

The counterpart of dead space in the lung is the volume from which gas exchange between capillaries and external air is carried out. In this exchange oxygen is introduced into the blood and carbon dioxide is provided to the pulmonary space. This space in which the gas exchange takes place has the structure of small vesicles that are called alveoli. The alveoli, where the gas exchange occurs, have an abundance of very small blood vessels, so-called capillaries. There is a tissue layer with a thickness of less than 1 μm between these capillaries and the air space of the alveoli. This is the so-called blood-air barrier. This is where the $O_2$ from the inhaled air is absorbed in the blood. This is due to the respiratory pigment hemoglobin which binds it. $CO_2$ is discharged from the blood into the air along the respective partial pressure gradient due to diffusion. $CO_2$ is present as $HCO_3^-$ in the blood.

FIG. 1 shows a schematic form of how respiratory air moves into the alveoli. External air 10 reaches the alveoli 14 via a respiratory tract 12. The exchange of the respiratory gases $O_2$ and $CO_2$ with the capillaries 16 of the blood system occurs in the alveoli.

An exchange of the respiratory gases $O_2$ and $CO_2$ always occurs in the alveoli. On the other hand ventilated alveoli can functionally become "dead space" if they are ventilated but are not surrounded sufficiently by blood. The ventilated portion of the lung is not a constant either. With an increase in breathing depth sections with additional dead space and additional exchange space are ventilated and vice versa. Even with maximum expiration a residual volume remains in the lung.

The so-called "physiological dead space" $x_{VD}$ is the dead space that takes up a new volume with each breath. On the other hand the so-called "anatomic dead space" is the sum of the volume of all anatomic structures of the respiratory tract that cannot participate in the gas exchange—regardless of whether they can currently be ventilated or not. The so-called breathing depth $x_{VT}$ is the entire gas volume of one single expiration. The exchange space or alveolar space ($x_{VA}$) thus is the difference between the breathing depth $x_{VT}$ and the physiological dead space $x_{VD}$:

$$x_{VA} = x_{VT} - x_{VD} \tag{1}$$

An expirogram shows the characteristic course of the concentration of the two respiratory gases $O_2$ and $CO_2$ during expiration as a function of volume and time. It is possible to determine the dead space of a lung using an expirogram. It can be used in different medical areas. For example, expirograms can provide a non-invasive method for recognizing pathologic changes in the lung. This can be useful for monitoring persons with a higher risk of pathological changes of the lung, such as hereditary risk factors or smokers. In addition, it is possible to monitor treatment progress using regular expirograms after a pathological change in the lung has been detected. A reduction of the tidal volume due to neuromuscular problems can be detected with expirograms as well.

Due to the anatomy of the lung the shapes of the expirograms show different, characteristic slopes, examples of which are shown in FIG. 2. FIG. 2 (a) through (e) show concentrations of respiratory gases $CO_2$ (left column) and $O_2$ (right column) measured at the mouth during expiration as a function of tidal volume of the exhaled air. At the beginning of the expiration (ref. FIG. 2(a)) the gas content flows from the mouth, pharynx and upper trachea past the mouth. There is no gas exchange through the alveoli in this tidal volume range so that the concentration distribution of the exhaled air corresponds to the composition of the room air that was previously inhaled. However, with increasing exhaled volume the share of the so-called alveolar air, i.e. the air from the exchange space of the lung, continuously increases at the mouth which causes the $CO_2$ concentration to increase and the $O_2$ concentration to decrease. FIGS. 2(b) through (d) show the increase in the $CO_2$ concentration associated with expiration from the increasingly deeper pulmonary regions and the corresponding decrease in $O_2$ concentration in the exhaled respiratory air. The gray inset schematically shows the pulmonary region of the lung 18 whose gas content contributes to the current expiration.

The more content of the dead space is flushed out, the closer the gas concentrations measured at the mouth are to the gas concentrations in the exchange space or alveolar space, respectively. As soon as the dead space is completely flushed out, the gas concentrations at the mouth correspond to the gas concentration in the alveolar space (ref. FIG. 2(e)). The alveolar gas concentration in turn changes in a linear manner in the course of the expiration compared to the tidal volume so that the curves of the expirogram for high tidal volumes change to a straight line. This linear course of the expirogram for $CO_2$ is due to the fact that a constant $CO_2$ flow mixes in with a decreasing alveolar volume—corresponding to expiration. The reverse applies to $O_2$. A constant flow of oxygen is removed from the increasingly decreasing alveolar volume. These linear shares of the expirograms often are called "alveolar slopes" due to their origin.

The information of the physiological space $x_{VD}$ of a breath are contained in the curves of any expirogram. The closer the measured gas concentration gets to the alveolar gas concentration, the more dead space is flushed out or the less dead space is not yet filled with alveolar air. If the course of the alveolar gas concentration is known, it is possible to determine the physiological dead space $x_{VD}$ from the distribution function until the alveolar gas concentration is reached. In this case the physiological dead space $x_{VD}$ corresponds to the mean flushing of the dead space with alveolar air.

To date there is no reliable, robust and numerically meaningful analysis method for determining the so-called "alveolar slopes".

Usually the method according to Fowler et al, which was introduced in 1948 in "The Respiratory Dead Space", Am J Physiol 154: pp. 405-416 is used to determine the physiological dead space $x_{VD}$. The method to determine the physiological dead space $x_{VD}$ according to Fowler is schematically shown in FIG. 3 for $CO_2$. To be able to determine the physiological dead space $x_{VD}$, the linear increase portion of the curve of the expirogram is fitted with a straight line. Using a surface comparison of the non-linear portion of the curve of the expirogram and using the previously determined fit straight line of the linear portion of the curve, the physiological dead space $x_{VD}$ is determined (measured in liters of tidal volume). The physiological dead space $x_{VD}$ is the tidal volume that is exhaled and in which the areas A and B shown in FIG. 3 have the same area. Due to the often problematic fitting of the straight line in the linear portion of the curve of expirograms, the customary Fowler method, however, is numerically especially sensitive so that a reliable analysis of the physiological dead space $x_{VD}$ from expirograms is possible only with reservations.

The object of the invention is to provide an apparatus for the acquisition and interpretation of expirograms that acquires and interprets expirograms in a numerically reliable, reproducible and robust manner in order to be able to determine and interpret the characteristic curves of expirograms. Another object of the invention is to provide a corresponding method as well as a corresponding computer program product.

These objects are attained by an apparatus with the features indicated in claim 1, a method that includes the steps indicated in claim 9 as well as a computer program product with the features indicated in claim 15. Preferred embodiments are the subject of the sub-claims.

According to the invention an apparatus for acquisition and interpretation of expirograms comprises:

a gas measuring probe that is designed to determine the gas concentration $f_{mess}$ of a gas in exhaled respiratory air;

a reading device that is connected to the gas measuring probe via signal and is designed to read for a plurality of values $x_1, \ldots, x_N$ of an exhaled volume of the exhaled respiratory air the respective determined gas concentrations $f_{mess}(x_1), \ldots, f_{mess}(x_N)$ from the gas measuring probe;

a storage device that is designed to store the values $x_1, \ldots, x_N$ assigned to the gas concentrations $f_{mess}(x_1), \ldots, f_{mess}(x_N)$;

a function fitting unit that is connected to the storage device via signal and that is designed to determine a non-linear fit function $$f(x)=g(x)\cdot h(x)+\text{Offset}_{Gas} \qquad (2)$$

for the stored gas concentrations $f_{mess}(x_1), \ldots, f_{mess}(x_N)$ by determining functions g(x) and h(x) wherein
h(x)=a+b·x g(x) is a continuously differentiable, non-linear function with $$g(0) = 0 \text{ and } \lim_{x \to \infty} g(x) = const,$$

a, b and const being constants and $\text{Offset}_{Gas}$ being a constant, mean concentration of the gas in room air.

Preferably the apparatus comprises a function fitting unit that is connected to the storage device via signal and that is designed to determine a non-linear fit function $f(x)=g(x)\cdot h(x)+\text{Offset}_{Gas}$ for the stored gas concentrations $f_{mess}(x_1), \ldots, f_{mess}(x_N)$ whereby h(x)=a+b·x g(x) is a continuously differentiable, non-linear function with g(0)=0 and g(x)=const for $x \geq x_{max}$, if the gas is carbon dioxide or, respectively, g(0)=const and g(x)=0 for $x \geq x_{max}$, if the gas is oxygen, a,b,const and $x_{max}$ being constants and $\text{Offset}_{Gas}$ being a constant, mean concentration of the gas in room air.

By means of the reading device and the measuring probe that is connected to it via signal, the respective gas concentrations $x_1, \ldots, x_N$ are determined for a plurality of volumes $f_{mess}(x_1), \ldots, f_{mess}(x_N)$ of an exhaled volume of the exhaled respiratory air in one breath. The gas measuring probe is designed to measure, directly at the mouth with sufficient repetition rate, the gas concentration $f_{mess}$ of a respiratory gas, i.e. oxygen $O_2$ or carbon dioxide $CO_2$ during a breath. The repetition rate preferably is at least 15 Hz, especially preferred at least 25 Hz. Preferably at least 15, further preferred at least 25 values N are acquired. The measured gas concentrations $f_{mess}(x_1), \ldots, f_{mess}(x_N)$ as well as the respective volume values $x_1, \ldots, x_N$ are saved in the storage device. The volume values preferably are calculated for each breath based on a measured gas flow Flow(t), i.e. of the volume of the exhaled respiratory air per unit of time and the volume value $x(t_i)$ at the time $t_i$ is the time integral across the measured gas flow Flow(t), i.e.

$$x_i = x(t_i) = \int_0^{t_i} Flow(t)\,dt$$

applies when the expiration occurs at the point in time t=0. The gas flow Flow(t) preferably is measured by way of a gas flow measuring probe that is designed to measure the gas flow in the immediate vicinity of the mouth. The function fitting unit accesses the gas concentrations $f_{mess}(x_1), \ldots, f_{mess}(x_N)$ and volume values $x_1, \ldots, x_N$ saved in the storage device in order to determine a non-linear fit function f(x).

According to the invention the fitting to the measuring data to the gas concentrations saved in the storage device is accomplished by means of a non-linear fit function f(x), which is the product of two functions with an offset. Both product terms of the fit function f(x) represent physiologically justified parts of the expirograms and allow for a surprisingly robust, reliable and numerically exact interpretation of the acquired expirogram.

The following paragraphs provide an exemplary explanation of how the function fitting unit as well as the non-linear fit function $f(x)$ function based on respiratory gas $CO_2$. All embodiments apply analogously to respiratory gas $O_2$.

According to the invention the non-linear fit function $f(x)$ contains a first product term $h(x)$ that describes the linear ascending curve portion of the expirogram for respiratory gas $CO_2$. The product term $h(x)$ thus has the equation of a straight line so that $$h(x) = a + b \cdot x \tag{3}$$

applies.

The second product term $g(x)$ of the non-linear fit function $f(x)$ represents the portion of the dead space flush until the 100% alveolar air concentration at the mouth is reached. The function $g(x)$ is a continuously differentiable function, i.e. a function whose first derivative following the tidal volume results in a continuous function which additionally must meet the following requirements:

If the respiratory gas is carbon dioxide, the value of the function for tidal volume 0 (start of expiration) equals 0. For large x the function $g(x)$ approaches a constant value. Above a certain tidal volume $x_{max}$ the function $g(x)$ preferably is a constant function for which preferably $g(x)=1$ for $x \geq x_{max}$ applies.

Between the volume value $x=0$ at which no air from the alveolar space reaches the mouth, up to the volume value $x_{max}$ at which an alveolar air concentration at the mouth of 100% is measured, function $g(x)$ preferably increases monotonically.

For respiratory gas $O_2$ a corresponding opposite course of function $f(x)$ is obtained. This opposite course is caused by an opposite preceding sign of the constant b from the linear function $h(x)$. In particular, the value of the function $f(x)$ for the tidal volume $x=0$ is a predetermined constant value.

The parameters a, b of the linear product term $h(x)$ as well as the limit volume $x_{max}$ represent constants that are to be determined during fitting. Furthermore, the non-linear fit function $f(x)$ has a constant offset that represents the (constant) mean concentration of the respective respiratory gas in the room air. The preceding sign of ascending gradient b of the left product term $h(x)$ of the non-linear fit function $f(x)$ is positive for respiratory gas $CO_2$ while it is negative for respiratory gas $O_2$.

Using a known fit algorithm, the function fitting unit is designed to approximate the saved, measured expirogram data $(x_1, \ldots, x_N; f_{mess}(x_1), \ldots, f_{mess}(x_N))$ by means of the non-linear fit function $f(x)$ that is defined in this manner. The measured gas concentration values $f_{mess}(x_i)$, after the fitting, materially correspond to the values $f(x_i)$ with $1 \leq i \leq N$ applying. Due to the non-linear fitting of the expirogram data by means of a product with the physiological justified product terms $g(x)$ and $h(x)$ a robust, simple and reproducible interpretation of shape characteristics of the acquired expirogram is possible.

According to an especially preferred embodiment the apparatus according to the invention furthermore comprises an evaluation unit that is designed to determine the physiological dead space $x_{VD}$ of a respective lung whereby $$\int_0^{x_{VD}} g(x) h(x) \, dx = \lim_{x_{max} \to \infty} \int_{x_{VD}}^{x_{max}} h(x)(1 - g(x)) \, dx \tag{4}$$

applies. The value of the function for the respiratory gas carbon dioxide is $f(0) = \text{Offset}_{CO_2}$.

Alternatively a preferred embodiment of the apparatus according to the invention comprises an evaluation unit that is designed to determine the physiological dead space $x_{VD}$ of a respective lung whereby $$\int_0^{x_{VD}} g(x) h(x) \, dx - f(0) x_{VD} = \int_{x_{VD}}^{x_{max}} h(x)(1 - g(x)) \, dx$$

applies.

Due to the stable function fitting by means of the non-linear fit function based on a product, the physiological dead space $x_{VD}$ of a respective lung, from which the respiratory air was exhaled, can be determined in a simple and numerically stable manner. The determination is based on an evaluation unit that is designed to solve the integral equation (4) based on the physiological dead space $x_{VD}$. It is possible to use all customary methods for the numerical solution of integral equations that are well-known in numerical mathematics.

Compared to customary methods for determining the physiological dead space $x_{VD}$ according to Fowler et al. the preferred apparatus according to the invention provides a considerably more accurate, reproducible determination of the physiological dead space $x_{VD}$ that is less dependent on the measuring quality of the expirogram data. This is primarily due to the selected product of the fit function $f(x)$ according to the invention that is made up of the product terms mentioned earlier. The preferred apparatus according to the invention allows for the automatic interpretation of a plurality of expirograms and the determination of the respective physiologic dead space $x_{VD}$ for each breath, i.e. for any expirogram.

Preferably function $g(x)$ is a monotonic function. The following applies especially preferred $$g(x) = \frac{k_4}{1 + \dfrac{e^{(k_1 \cdot c - k_1 \cdot x)}}{1 + e^{\left(-\frac{2 k_1 \cdot c k_2}{|k_1 + k_2|} + \frac{2 k_1 \cdot k_2 \cdot x}{|k_1 + k_2|}\right)}} - \dfrac{e^{(k_2 \cdot c - k_2 \cdot x)}}{1 + e^{\left(-\frac{2 k_1 \cdot c k_2}{|k_1 + k_2|} + \frac{2 k_1 \cdot k_2 \cdot x}{|k_1 + k_2|}\right)}} + e^{(c \cdot k_2 - k_2 x)}} + k_3 \tag{5}$$

and most preferred $$g(x) = \frac{1}{1 + \dfrac{e^{(k_1 \cdot c - k_1 \cdot x)}}{1 + e^{\left(-\frac{2 k_1 \cdot c k_2}{|k_1 + k_2|} + \frac{2 k_1 \cdot k_2 \cdot x}{|k_1 + k_2|}\right)}} - \dfrac{e^{(k_2 \cdot c - k_2 \cdot x)}}{1 + e^{\left(-\frac{2 k_1 \cdot c k_2}{|k_1 + k_2|} + \frac{2 k_1 \cdot k_2 \cdot x}{|k_1 + k_2|}\right)}} + e^{(c \cdot k_2 - k_2 x)}} + k_3$$

with $k_1$, $k_2$, $k_3$, $k_4$ and c being constants. $k_3$ and $k_4$ preferably are selected such that $$g(0) = 0 \text{ and } \lim_{x \to \infty} g(x) = 1 \text{ applies.}$$

$k_1$ represents the steepness of the lower curve portion, $k_2$ the steepness of the upper curve portion and c the position of the curve in x direction. The term $k_3$ preferably is selected such that g(0)=0 applies. In turn, x is the current tidal volume that is exhaled within one breath with an application as a function of time of expiration being possible.

Alternatively the following preferably applies $$g(x) = \cfrac{1}{1 + \cfrac{e^{(k_1 \cdot c - k_1 \cdot x)}}{1 + e^{\left(-\frac{2k_1 \cdot c k_2}{|k_1 + k_2|} + \frac{2k_1 \cdot k_2 \cdot x}{|k_1 + k_2|}\right)}} - \cfrac{e^{(k_2 \cdot c - k_2 \cdot x)}}{1 + e^{\left(-\frac{2k_1 \cdot c k_2}{|k_1 + k_2|} + \frac{2k_1 \cdot k_2 \cdot x}{|k_1 + k_2|}\right)}} + e^{(c \cdot k_2 - k_2 \cdot x)}}$$

with $k_1$, $k_2$ and c being constants.

The average steepness of the curved portions of the expirogram is based on the completed non-linear fitting of $$Steilheit = \frac{2 \cdot k_1 \cdot k_2}{|k_1 + k_2|} \quad (6)$$

Preferably the function fitting unit is designed to determine the fit function $f(x)=g(x) \cdot h(x)+\text{Offset}_{Gas}$ according to the Marquardt-Levenberg Algorithm. It was found that according to the Marquardt-Levenberg Algorithm an especially good non-linear fitting of the fit function to the acquired expirogram data is possible.

Preferably the storage device is an electronic storage device. In particular, the electronic storage device can be a volatile or non-volatile semiconductor storage or, for example, a magnetic storage medium such as a computer hard drive.

According to another preferred embodiment the apparatus according to the invention furthermore comprises an evaluation device that is designed to calculate the alveolar recruitment rate g'(x) by deviating the function g(x) based on the exhaled volume x.

The alveolar recruitment rate g'(x) is the name for the rate of the alveolar space that is added for tidal volume x for emptying. The higher the value for g'(x), the more gas from the alveolar space has flushed the respective dead space when this volume is exhaled. Such an interpretation and determination of the alveolar recruitment rate g'(x) is of material significance, in particular for scientific and also non-diagnostic purposes.

The graphic representation and numeric scaling of the alveolar recruitment rate g'(x) represents significant additional and important information. In particular it is possible to diagnose different pathological and physiological changes in the lung based on this form of presentation. Changes in the breathing mechanics or pulmonary anatomy would have a direct impact on the alveolar recruitment rate. Preferably the display device is a monitor on which the alveolar recruitment rate is displayed, preferably simultaneously with or shortly after the acquisition of the measured values. In this context "shortly after" preferably means within five seconds after the completion of the acquisition of the measured data, especially preferred within one second after the completion of the acquisition of the measured data.

According to another especially preferred embodiment the apparatus according to the invention furthermore comprises a display unit that is designed to provide a graphic display of the alveolar recruitment g'(x).

According to another aspect of the invention an apparatus for acquisition and interpretation of expirograms comprises:
- a gas flow measuring probe that is designed to determine the gas flow Flow(t) (i.e. of an inhaled or exhaled respiratory air volume per unit of time) of respiratory air as a function of breathing time t;
- a gas measuring probe that is designed to determine the gas concentration $f_{mess}(t)$ of a gas in inhaled or exhaled respiratory air;
- a breathing recognition unit that is designed to recognize the beginning $x_B$ of an inhalation based on the determined gas flow Flow(t);
- an extremes recognition unit that is designed to recognize values $t_{Extrema}$ for which $f_{mess}(t_{Extrema})$ represent extremes based on the determined gas concentration $f_{mess}(t)$;
- a synchronization unit that synchronizes the recognized beginning $t_B$ of the inhalation with the respective recognized value $t_{Extrema}=t_B+\Delta t$ of the determined gas concentration by shifting the determined gas flow Flow(t) or shifting the determined gas concentration $f_{mess}(t)$ by an amount $\Delta t$.

The determination of the gas flow Flow(t) and the gas concentration $f_{mess}(t)$ can be based on a plurality of discrete values $t_1, \ldots, t_N$ so that continuous acquisition is not necessary. The values $t_1, \ldots, t_N$ represent breathing times whereby the point in time t=0 indicates the beginning of an expiration of a breath and $t=t_B$ the beginning of the subsequent inhalation, for example. Equally, the above correlations can also be shown as a function of the volumes of the exhaled respiratory air. The volume values $x_i$ preferably are calculated for each breath based on a measured gas flow, Flow(t) i.e. of the volume of the exhaled respiratory air per unit of time and the volume value $x(t_i)$ at the time $t_i$ is the time integral across the measured gas flow Flow(t) i.e.

$$x_i = x(t_i) = \int_0^{t_i} Flow(t) \, dt$$

applies when the expiration occurs at the point in time t=0.

The gas flow measuring probe preferably is arranged directly at the candidate's mouth and acquires the gas flow Flow(t), i.e. the inhaled or exhaled tidal volume per unit of time (unit liter/s), as a function of the breathing time t or the tidal volume, respectively. The breathing recognition unit is designed to recognize the beginning $t_B$ of the inhalation based on the determined gas flow Flow(t) with preferably $$Flow(t_B) = 0 \text{ and } \left.\frac{\partial Flow(t)}{\partial t}\right|_{t_B} > 0$$

(zero of the ascending flank of Flow(t)). The extreme recognition unit is designed to recognize or determine those values $t_{Extrema}$ for which $f_{mess}(t_{Extrema})$ show extremes. For carbon dioxide the extremes represent maximums (highest carbon dioxide concentration at the end of expiration), while the extremes are minimum values for oxygen (lowest oxygen concentration at the end of expiration). The extremes coincide with the steep decline of the carbon dioxide concentration or with the steep incline of the oxygen concentration of $f_{mess}(t)$ respectively.

Preferably such a synchronization of the determined gas flow Flow(t) occurs with the determined gas concentration $f_{mess}(t)$ for each breath. Thus it was found that surprisingly the delay $\Delta t$ is unstable in regard to time due to various variables, especially air pressure, breathing action, and humidity, and can be subject to distinct fluctuations. The physical cause for the delay $\Delta t$ in particular is due to the fact that the gas flow Flow(t) and the gas concentration $f_{mess}(t)$ often cannot be measured at the same location. For example, the gas flow Flow(t) can be measured in the immediate vicinity of the mouth while measuring the gas concentration requires a larger measuring probe that is arranged at a distance and which requires additional tubes and hoses for the respiratory air.

This aspect of the invention advantageously can be combined in connection with the above devices according to the invention for acquiring and interpreting expirograms.

According to the invention a method for the acquisition and interpretation of expirograms comprises the following steps:

Measuring of gas concentrations $f_{mess}(x_1), \ldots, f_{mess}(x_N)$ for a plurality of values $x_1, \ldots, x_N$ of an exhaled volume of exhaled respiratory air;

Saving of the measured gas concentrations of the $x_1, \ldots, x_N$ respective values $f_{mess}(x_1), \ldots, f_{mess}(x_N)$;

Determination of a non-linear fit function $f(x) = g(x) \cdot h(x) + \text{Offset}_{Gas}$ for the stored gas concentrations $f_{mess}(x_1), \ldots, f_{mess}(x_N)$ by determining functions g(x) and h(x)
wherein
$h(x) = a + b \cdot x$
g(x) is a continuously differentiable, non-linear function with $$g(0) = 0 \text{ and } \lim_{x \to \infty} g(x) = const,$$

a, b and const being constants and
$\text{Offset}_{Gas}$ being a constant, mean concentration of the gas in room air.

Preferably the method comprises the determination of a non-linear fit function $f(x) = g(x) \cdot h(x) + \text{Offset}_{Gas}$ for the stored gas concentrations $f_{mess}(x_1), \ldots, f_{mess}(x_N)$ wherein
$h(x) = a + b \cdot x$
g(x) is a continuously differentiable, non-linear function with
$g(0) = 0$ and $g(x) = const$ for $x \geq x_{max}$, if the gas is carbon dioxide or, respectively,
$g(0) = const$ and $g(x) = 0$ for $x \geq x_{max}$, if the gas is oxygen,
a, b, const and $x_{max}$ being constants and
$\text{Offset}_{Gas}$ being a constant, mean concentration of the gas in room air.

With regard to the characteristics, features and advantages of the method according to the invention we refer to the description of the apparatus according to the invention and its preferred embodiments. Characteristics that were described only in connection with the apparatus according to the invention can also be applied to the method according to the invention.

The execution of the method according to the invention does not require that the user have medical knowledge so that personnel with no or little medical knowledge can execute the method. The acquired data can be used for scientific, non-diagnostic purposes as well as for the subsequent diagnosis by a physician.

Preferably the method according to the invention furthermore comprises the step of determining the physiological dead space $x_{VD}$ of a respective lung wherein $$\int_0^{x_{VD}} g(x) h(x) \, dx = \lim_{x_{max} \to \infty} \int_{x_{VD}}^{x_{max}} h(x)(1 - g(x)) \, dx \qquad (7)$$

applies.

Alternatively the method according to the invention preferably comprises the step for determining the physiological dead space $x_{VD}$ of a respective lung wherein $$\int_0^{x_{VD}} g(x) h(x) \, dx - f(0) x_{VD} = \int_{x_{VD}}^{x_{max}} h(x)(1 - g(x)) \, dx$$

applies.

Preferably the following applies $$g(x) = \frac{1}{1 + \dfrac{e^{(k_1 \cdot c - k_1 \cdot x)}}{1 + e^{\left(-\frac{2k_1 \cdot k_2}{|k_1 + k_2|} + \frac{2k_1 \cdot k_2 \cdot x}{|k_1 + k_2|}\right)}} - \dfrac{e^{(k_2 \cdot c - k_2 \cdot x)}}{1 + e^{\left(-\frac{2k_1 \cdot k_2}{|k_1 + k_2|} + \frac{2k_1 \cdot k_2 \cdot x}{|k_1 + k_2|}\right)}} + e^{(c \cdot k_2 - k_2 x)}} + k_3, \qquad (8)$$

with $k_1$, $k_2$, $k_3$ and c being constants.

Alternatively the following preferably applies $$g(x) = \frac{1}{1 + \dfrac{e^{(k_1 \cdot c - k_1 \cdot x)}}{1 + e^{\left(-\frac{2k_1 \cdot k_2}{|k_1 + k_2|} + \frac{2k_1 \cdot k_2 \cdot x}{|k_1 + k_2|}\right)}} - \dfrac{e^{(k_2 \cdot c - k_2 \cdot x)}}{1 + e^{\left(-\frac{2k_1 \cdot k_2}{|k_1 + k_2|} + \frac{2k_1 \cdot k_2 \cdot x}{|k_1 + k_2|}\right)}} + e^{(c \cdot k_2 - k_2 x)}}, \qquad (8)$$

with $k_1$, $k_2$ and c being constants.

According to a preferred variation of the method according to the invention the step of determining the fit function $f(x) = g(x) \cdot h(x) + \text{Offset}_{Gas}$ comprises a Marquardt-Levenberg Algorithm.

Especially preferred, the method according to the invention furthermore comprises the step of calculating the alveolar recruitment rate g'(x) by deriving the function g(x). Preferably the alveolar recruitment rate g'(x) is graphically displayed on a display device.

According to the invention a computer program product or computer program model for interpreting expirograms requires program steps for carrying out a method with the following steps:

Entering gas concentrations $f_{mess}(x_1), \ldots, f_{mess}(x_N)$ for a plurality of values $x_1, \ldots, x_N$ of an exhaled volume of exhaled respiratory air;

Saving of the measured gas concentrations of the $x_1, \ldots, x_N$ respective values $f_{mess}(x_1), \ldots, f_{mess}(x_N)$;

Determination of a non-linear fit function $f(x) = g(x) \cdot h(x) + \text{Offset}_{Gas}$ for the stored gas concentrations $f_{mess}(x_1), \ldots, f_{mess}(x_N)$ by determining functions g(x) and h(x)
wherein
h(x)=a+b·x
g(x) is a continuously differentiable, non-linear function with $$g(0) = 0 \text{ and } \lim_{x \to \infty} g(x) = const,$$

a, b and const being constants and
$Offset_{Gas}$ being a constant, mean concentration of the gas in room air.

Preferably the computer program product comprises program steps for determining a non-linear fit function $$f(x)=g(x)\cdot h(x)+Offset_{Gas}$$

for the stored gas concentrations $f_{mess}(x_1), \ldots, f_{mess}(x_N)$
wherein
h(x)=a+b·x
g(x) is a continuously differentiable, non-linear function with g(0)=0 and g(x)=const for $x \geq x_{max}$, if the gas is carbon dioxide or, respectively,
g(0)=const and g(x)=0 for $x \geq x_{max}$, if the gas is oxygen,
a, b, const and $x_{max}$ being constants and
$Offset_{Gas}$ being a constant, mean concentration of the gas in room air.

Preferably the computer program product according to the invention comprises program steps for carrying out a method that comprises the step of determining the physiological dead space $x_{VD}$ of a respective lung wherein $$\int_0^{x_{VD}} g(x)h(x)dx = \lim_{x_{max} \to \infty} \int_{x_{VD}}^{x_{max}} h(x)(1-g(x))dx$$

applies.

Alternatively the computer program product according to the invention preferably comprises program steps for carrying out a method that comprises the step of determining the physiological dead space $x_{VD}$ of a respective lung wherein $$\int_0^{x_{VD}} g(x)h(x)dx - f(0)x_{VD} = \int_{x_{VD}}^{x_{max}} h(x)(1-g(x))dx$$

applies.

With regard to the characteristics, advantages and features of the computer program product according to the invention we refer to the above description of the method according to the invention as well as the description of the apparatus according to the invention and their preferred embodiments. Characteristics that were described only in connection with the method according to the invention or the apparatus according to the invention can also be applied to the computer program product according to the invention.

The inventive concept of synchronizing the gas flow Flow (x) with the gas concentration $f_{mess}(x)$ can advantageously be used for the method according to the invention as well as for the computer program products according to the invention. In particular, the calculation of the delay Δx preferably is carried out for each breath.

The invention is explained based on examples and the accompanying drawings. The FIG.ures show the following:

FIG. 4 shows an example of an experimental course of the $CO_2$ concentration as a function of the exhaled tidal volume while;

FIG. 4(a) shows the linear product term h(x) of the non-linear fit function f(x) after the fitting of the expirogram data;

FIG. 4(b) shows the non-linear product term g(x) of the non-linear fit function f(x) after the fitting of the expirogram data;

FIG. 4(c) shows the non-linear fit function f(x) the offset-corrected product of functions h(x) and g(x);

Figure 1:
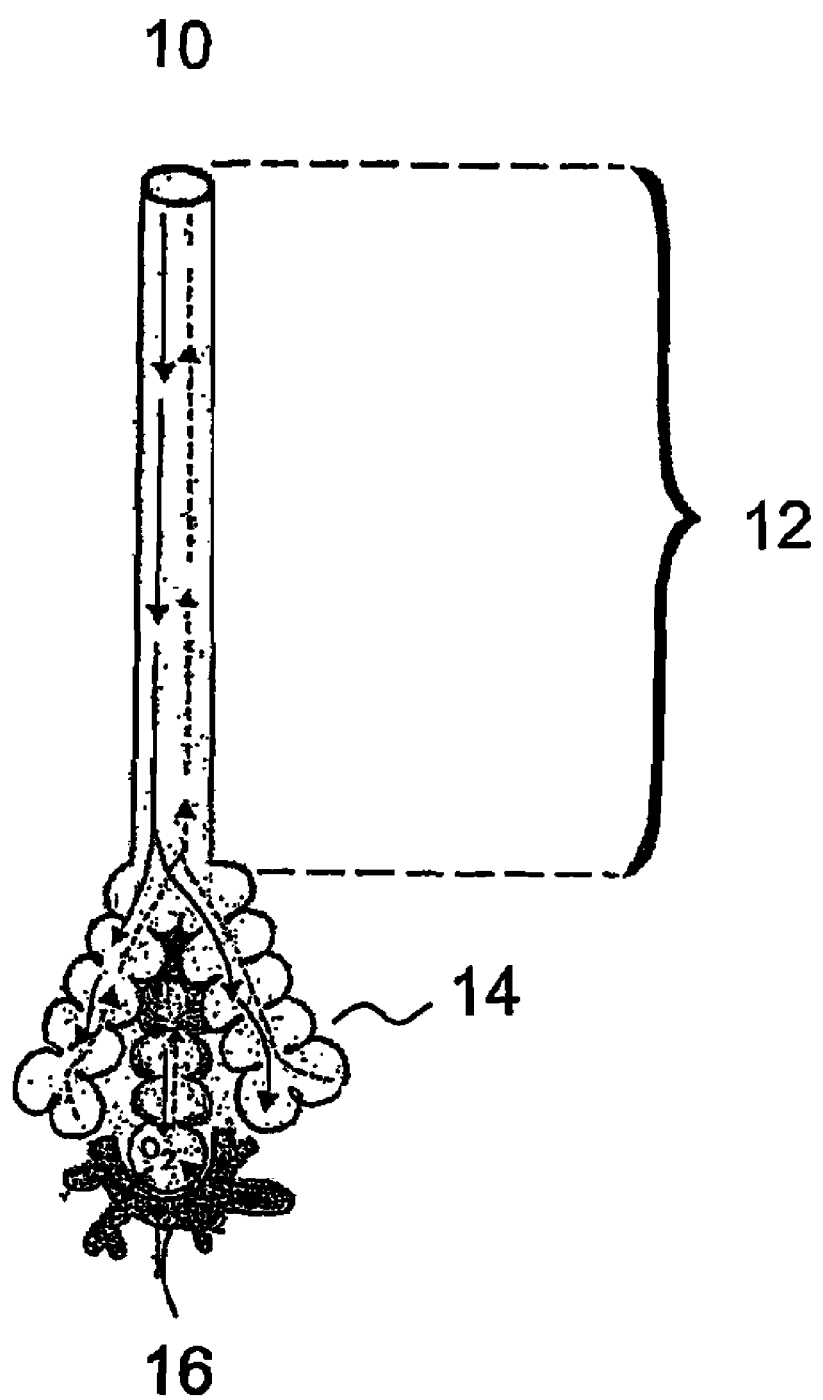
FIG. 1 shows a diagram of the path of respiratory air into the alveoli.
Figure 2:
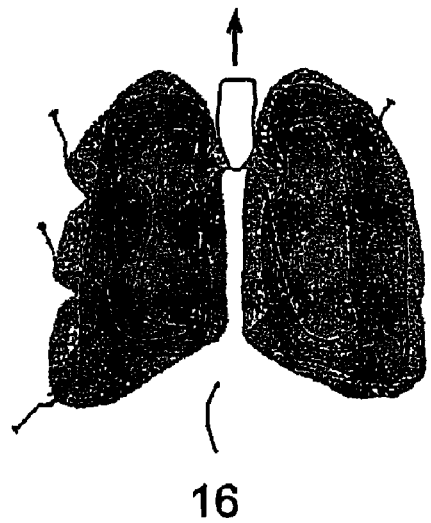
FIG. 2 shows the concentration of respiratory gases $O_2$ and $CO_2$ measured at the mouth during expiration as a function of the exhaled air wherein the left graph column shows the course for respiratory gas $CO_2$ and the right graph column shows the course for respiratory gas $O_2$.
Figure 2:
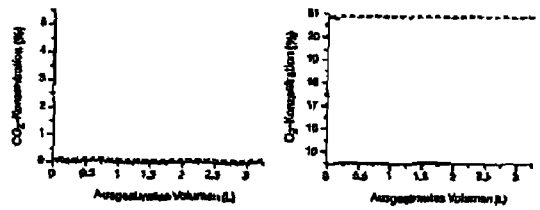
Figure 2:
Figure 2:
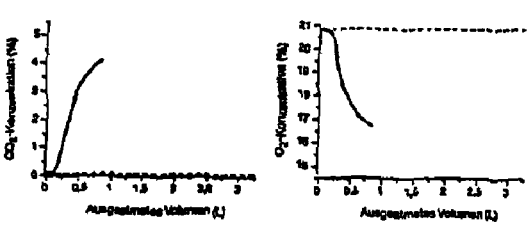
Figure 2:
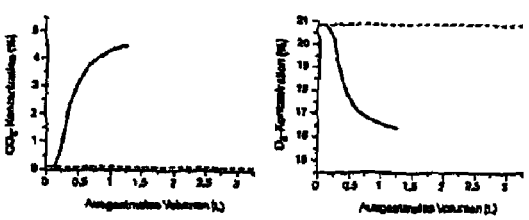
Figure 2:
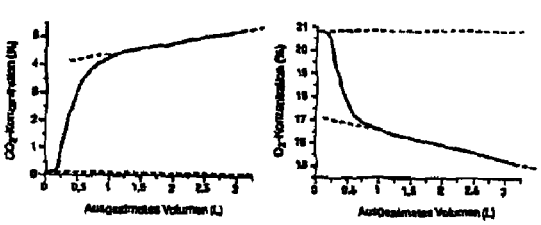
Figure 3:
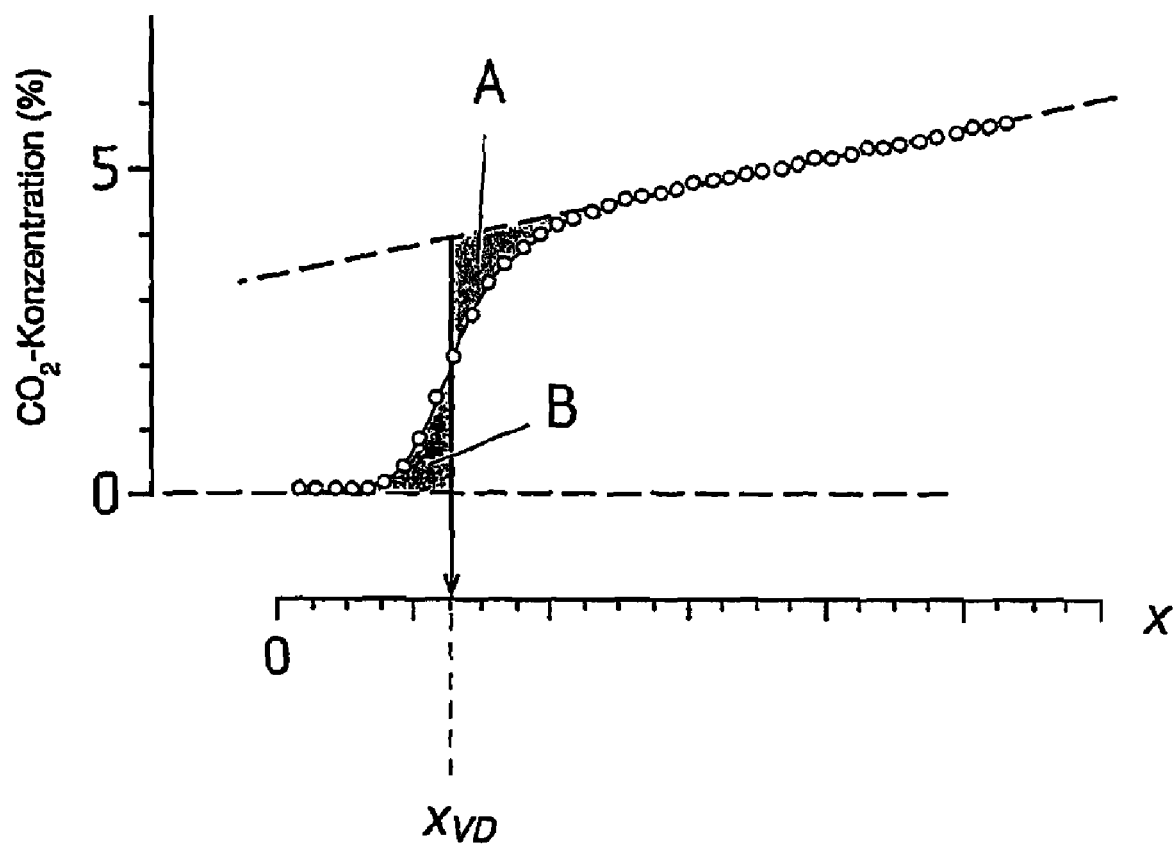
FIG. 3 shows an example of a measured course of the $CO_2$ concentration as a function of the exhaled volume of respiratory air as well as a fit line for determining the physiological dead space $x_{VD}$ according to Fowler et al.
Figure 4:
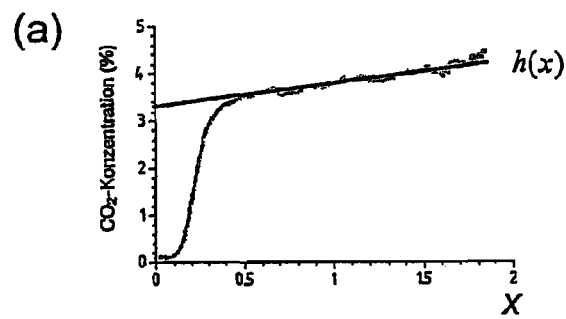
Figure 4:
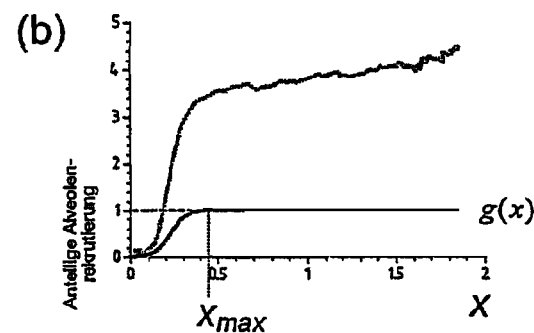
Figure 4:
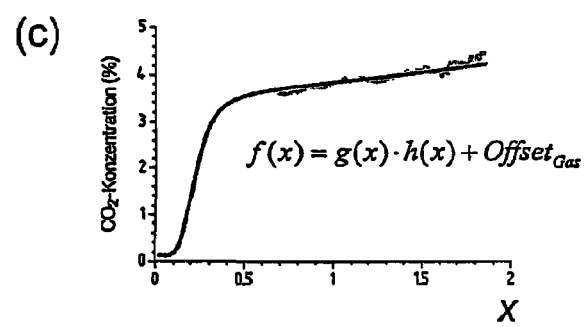
Figure 5:
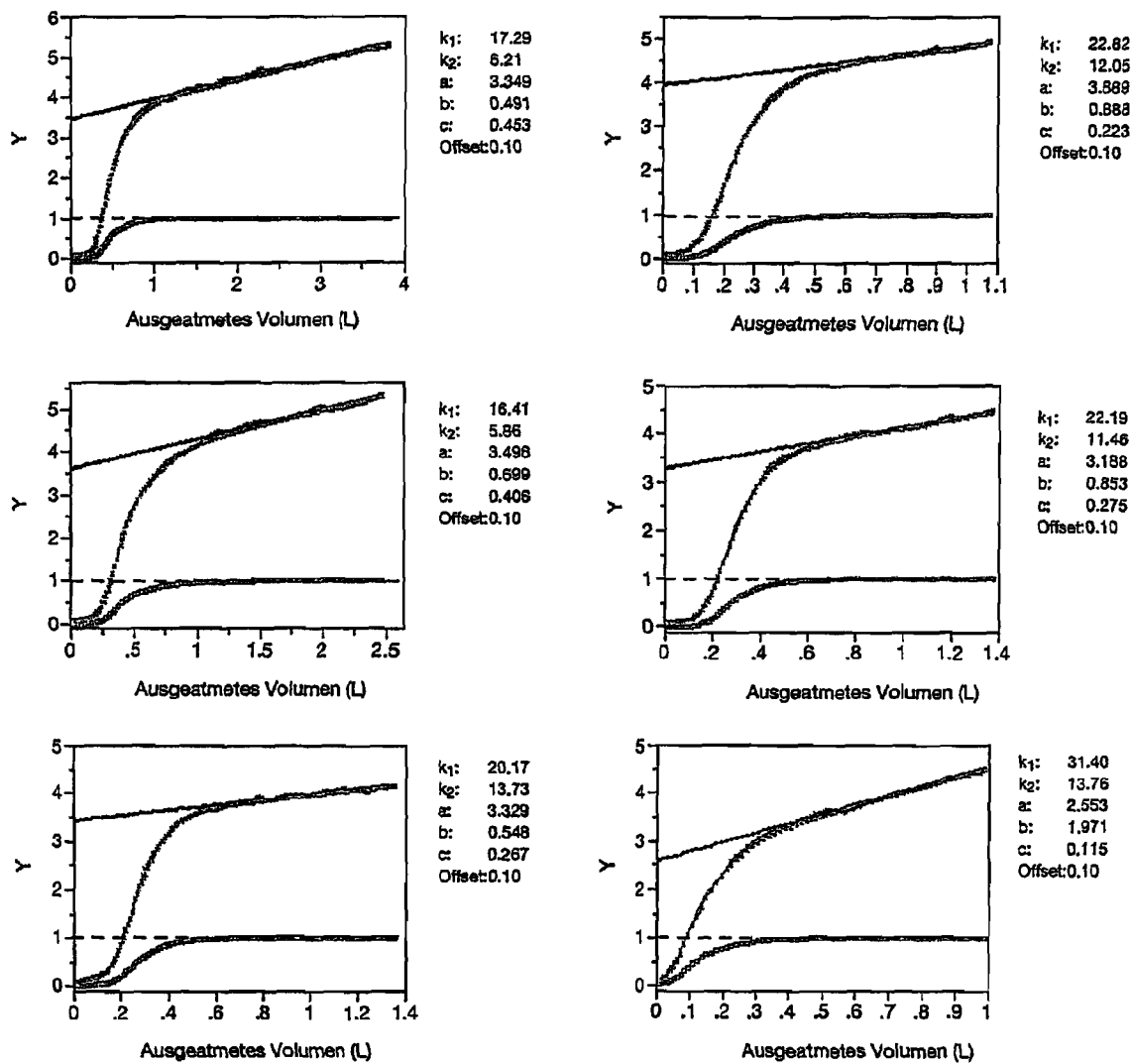
FIG. 5 shows six randomly selected individual examples of expirograms together with the product terms h(x) and g(x) of the fit function f(x) after the fitting is complete with the fit parameters being indicated next to the respective expirograms.

FIG. 4 shows the execution of a preferred variation of the method according to the invention based on an example of an expirogram for respiratory gas $CO_2$ that was obtained experimentally. The experimentally determined expirogram data, i.e. the $CO_2$ concentration measured at the mouth as a function of the exhaled tidal volume, are fitted by a non-linear fit function f(x), which is comprised of a physiologically justified product use and a constant offset.

As can be seen in FIG. 4(a), the linear function h(x), after fitting is completed, describes the approximate expirogram data in the linear slope of the curve of the expirogram, i.e. in the area of the "alveolar slope". The second product term of the product of the fit function f(x), i.e. the non-linear function g(x), represents the pro-rated alveolar recruitment. Function g(x) preferably is a double sigmoid function that ascends in a monotonic manner and is continuously differentiable. FIG. 4(c) shows an overlap of the measured expirogram data and the fit function $f(x)$.

Especially the numerically robust calculation of the physiological dead space $x_{VD}$ from breath to breath provides clear information for pulmonology, intensive care medicine, emergency medicine, physiology, sports medicine, and occupational medicine. Clinical pictures such as asthma (constriction of the respiratory tract during attacks), atelectasis (acute obstruction of respiratory tracts, especially patients on ventilators), pulmonary embolism (acute obstruction of pulmonary blood vessels) or even ineffective respiratory mechanics during physical exertion have an impact on the physiological dead space $x_{VD}$ or the ratio $x_{VT}/x_{VD}$.

However, other shape characteristics of expirograms are of basic, non-diagnostic interest. This, for example, includes the ascend of the "alveolar slopes" b or the actual course of the alveolar gas concentration based on $h(x)$. Furthermore, the exponential characteristic of the curved portion of the expirograms either as a function of time or as a function of volume is useable for scientific or diagnostic purposes.

The special feature of the multiplicative separation of the two product shares of the fit function $f(x)$ according to the invention on one hand is due to the numerical scaling of the physiologic base and on the other hand due to the better possibility of non-linear fitting. Up until now applications for the automated interpretation of "alveolar slopes" and physiological dead space $x_{VD}$ attempted a direct extraction of the linear shares of the expirograms. However, this approach usually is not satisfactory due to the lack of unambiguousness of the limit between the linear and the curved section of expirograms.

The invention on the other hand provides a numerically stable, reproducible and robust interpretation of expirograms. This is shown based on six random examples of experimentally determined expirograms and the respective fits according to a preferred method according to the invention in FIG. 5. FIGS. 5(a) through (f) show the experimental expirograms together with the linear product term $h(x)$ and the non-linear product term $g(x)$. The parameters resulting from the non-linear fitting are shown next to the respective sample graphs.

The optimization of the function parameters in curve fitting to the course of the measured expirogram data can be obtained by applying different, established methods. Preferred is a parameter optimization with the help of the Marquardt-Levenberg method. The robustness of the parameter optimization according to the Marquardt-Levenberg method decreases with an increase in the number of parameters. Conversely, the method becomes more robust the more exact the estimated starting values are near the actual optimum. According to an especially preferred method of the invention the method according to the invention therefore is implemented in a manner that ensures that it transitions gradually from the most simple model for the determination of the "alveolar slopes" to the more complex models with an increasing number of parameters with the resulting parameters being transferred to the next, more complex model as a starting value.

The gas measuring probe of an apparatus according to the invention, for example, can be a gas sensor functioning on the basis of respiratory mass spectroscopy. The technical application of the method according to the invention or an apparatus according to the invention can also be carried out with other methods of continuous gas analysis and gas volume measuring. In particular, multiple and simple methods are available for carbon dioxide concentration measuring in respiratory air. A data acquisition rate of 25 Hertz or more is preferred for clean measuring data acquisition of expirograms.

Figure 6:
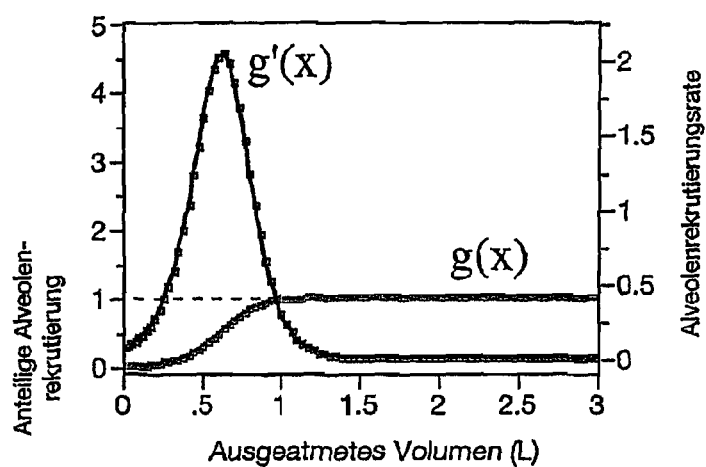
FIG. 6 shows the pro-rated alveolar recruitment g(x) as well as the alveolar recruitment rate g'(x) applied to the exhaled volume within one breath for the exhaled $CO_2$ concentration.

FIG. 6 shows the pro-rated alveolar recruitment $g(x)$ as a function of the exhaled volume as well as the first derivative of $g(x)$ that represents the alveolar recruitment rate $g'(x)$. $g(x)$ describes the share of the alveolar space that started at volume x and that is emptied during expiration. The more alveolar space is recruited in this manner, the more dead space was flushed by alveolar air, the closer the value $g(x)$ is near a constant value, which preferably equals 1. $g(x)=1$ means that 100% of the dead space was flushed by alveolar air and that at this moment the actual gas concentration of the alveoli can be measured without any falsifications due to the interference of dead space air. The alveolar recruitment rate $g'(x)$ is the name for the rate of the alveolar space that is to be emptied at volume x. The higher the value for $g'(x)$, the more gas from the alveolar space has flushed the respective dead space when this volume is exhaled.

The graphic illustration and numerical scaling of the alveolar recruitment rate $g'(x)$ means that considerably more information is available since different pathological or physiological changes in the lung can be diagnosed from this presentation. Changes in the breathing mechanics or pulmonary anatomy would have a direct impact on the alveolar recruitment rate $g'(x)$.

An intuitively acquired presentation in the sense of a "visual pulmonary index" is especially preferred and is provided based on the alveolar recruitment rate $g'(x)$. In such a preferred graphic presentation the distribution of the dead space, i.e. the "distance" of the respective alveoli to the mouth is shown.

Figure 7:
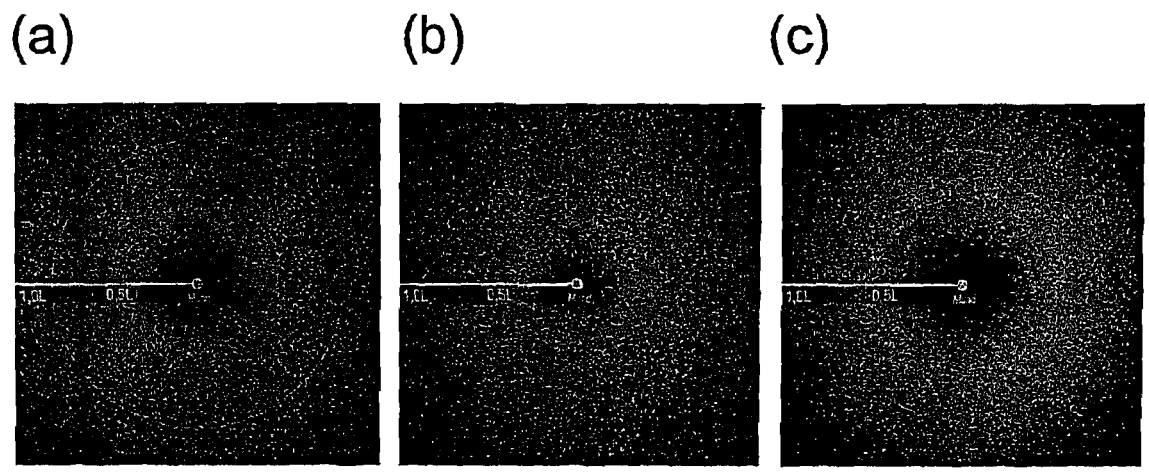
FIG. 7 shows examples of a "visual pulmonary index" as a graphic presentation of the alveolar recruitment rate g'(x) with the alveolar recruitment rate g'(x) being presented as density distribution of a circle whose radius presents the amount of g'(x)

A preferred graphic presentation of the alveolar recruitment rate $g'(x)$ shows the symbolic transfer of the information from $g'(x)$ to the density of points arranged inside the circle, as shown in FIG. 7. The point density at a certain distance to the center of the graphic represents the probability of the location of alveoli/exchange space $x_{VD}$ and therefore provides visual information concerning the physiological dead space $x_{VD}$ and the distribution of this dead space within the lung with each breath. The dispersion of the randomly distributed points thus represents the distribution of the alveolar space recruitment.

Especially advantageous would be a continuous or close to real-time calculation and graphic representation of the alveolar recruitment rate $g'(x)$ for monitoring purposes, for example for patients on a ventilator. An obstruction or constriction of the respiratory tract or stenosis of the respiratory tract due to a so-called bronchial constriction would be visible prima vista due to the changed shape. Other areas of application are exams concerning the reaction to physical stress in sports medicine or occupational medicine, bronchial provocation tests in pulmonology, comparison exams for chronic obstructive pulmonary disease (COPD) or emphysema. The described method is special in that it is not necessary to carry out any respiratory maneuvers. This advantageously results in the absence of the insecurity factor in regard to cooperation of the candidate and the motivation of the candidate.

The graphic display as it is shown in FIG. 7, for example, preferably can be complemented by different base information that can be made visible my marking the graphics correspondingly (breath by breath). Preferred would be the inclusion of at least one piece of the following, additional base information:
physiological dead space:
    sliding mean value for separation comparison
    maximum value (can be reset)

minimum value (can be reset)
different percentile stages of the alveolar space recruitment (for example 5, 25, 75, 90)
maximum breathing depth $x_{VT}$ These values can be superimposed on the above diagram in the form of a color transparency, for example. The graphic implementation of the alveolar recruitment rate g'(x) for a visual pulmonary index, however, can also be carried out with other graphic, intuitively acquired forms of presentation. Apart from an especially suggestive circle shape, it also is possible to distribute the calculated information on the image of a lung or on any other two-or three-dimensional shape. A presentation in the form of a histogram can be advantageous as well. Apart from the linear scaling of the area to be shown, it would also be useful to use a logarithm scale for presentation purposes.

Apart from the "online" presentation for the alveolar recruitment rate that is close to real-time g'(x) an "offline" documentation of the breaths may be advantageous as well. It lists the results graphics of the "visual pulmonary index" in a printout or an image file. This allows for a subsequent interpretation of the changes in the course of time. Comparison lines are applied over the listing on the printout or in image files, e.g. in the area of the value of the average physiological dead spaces $x_{VD}$. This makes changes visible at one glance.

Figure 8:
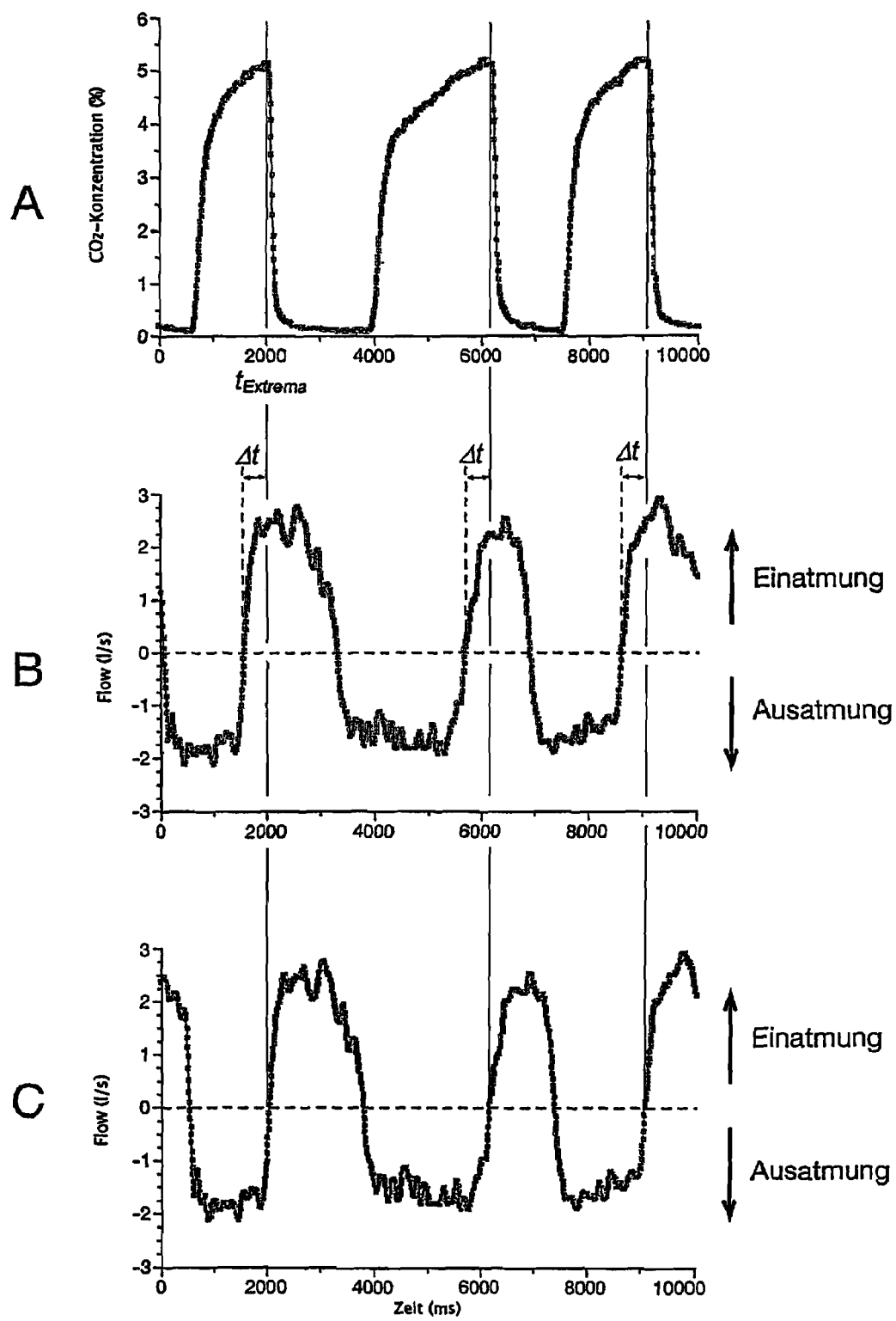
FIG. 8A shows an example of a measured carbon dioxide concentration $f_{mess}$ in respiratory air as a function of time across several breaths.
FIG. 8B shows a measured "non-corrected" gas flow Flow as a function of time that is delayed by a delay Δx with regard to the gas concentration $f_{mess}$.
FIG. 8C shows the gas flow $f_{mess}$ that is synchronized with the carbon dioxide concentration Flow with regard to time.

FIG. 8 shows in more detail another aspect of the invention which refers to the synchronization of the measured gas flow Flow(t) with the gas concentration $f_{mess}(t)$. FIG. 8A shows the measured carbon dioxide concentration in respiratory air for three breaths as a function of time. The application of FIG. 8 could also be used for the tidal volume.

The respective gas flow of the respiratory air measured at the mouth is shown in FIG. 8B. The gas flow is shifted by an amount $\Delta t$ especially due to different distances from tubes or hoses for the respiratory air to the gas measuring probe for measuring the gas concentration and to the gas flow measuring probe for measuring the gas flow. According to the invention it is proposed to synchronize the gas flow Flow(t) with the gas concentration $f_{mess}(t)$ in particular for every breath so that the zero point $t_B$ of the ascending flank of the gas flow Flow(t) coincides with the respective value $t_{Extrema}$ at which $f_{mess}(t)$ shows a maximum.

Figure 9:
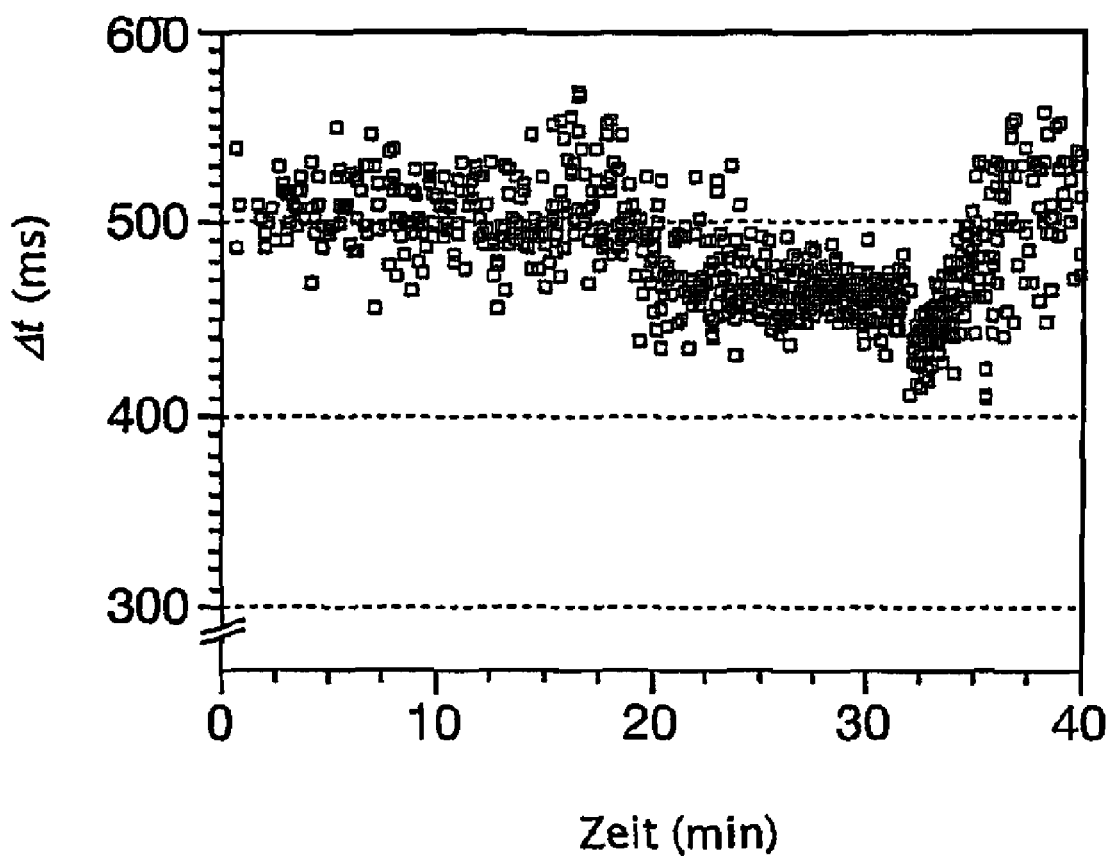
FIG. 9 shows a graph that shows examples of the values of the delay Δt in the course of a stress test as a function of time.

FIG. 9 shows a graph that shows examples of the values of the delay $\Delta x$ in the course of a stress test as a function of time. The scattering of the delay $\Delta t$ from breath to breath is clearly visible so that it is advantageous to determine the values breath by breath.

An especially advantageous application of the apparatus, methods and computer program products according to the invention is the monitoring of the scattering of the ventilation of comatose patients or patients under anesthesia. The invention especially allows for better adjustment of a gentle, i.e. "protective" ventilation since the automated expirogram analysis would make any changes to the pulmonary mechanics visible right away.

Figure 10:
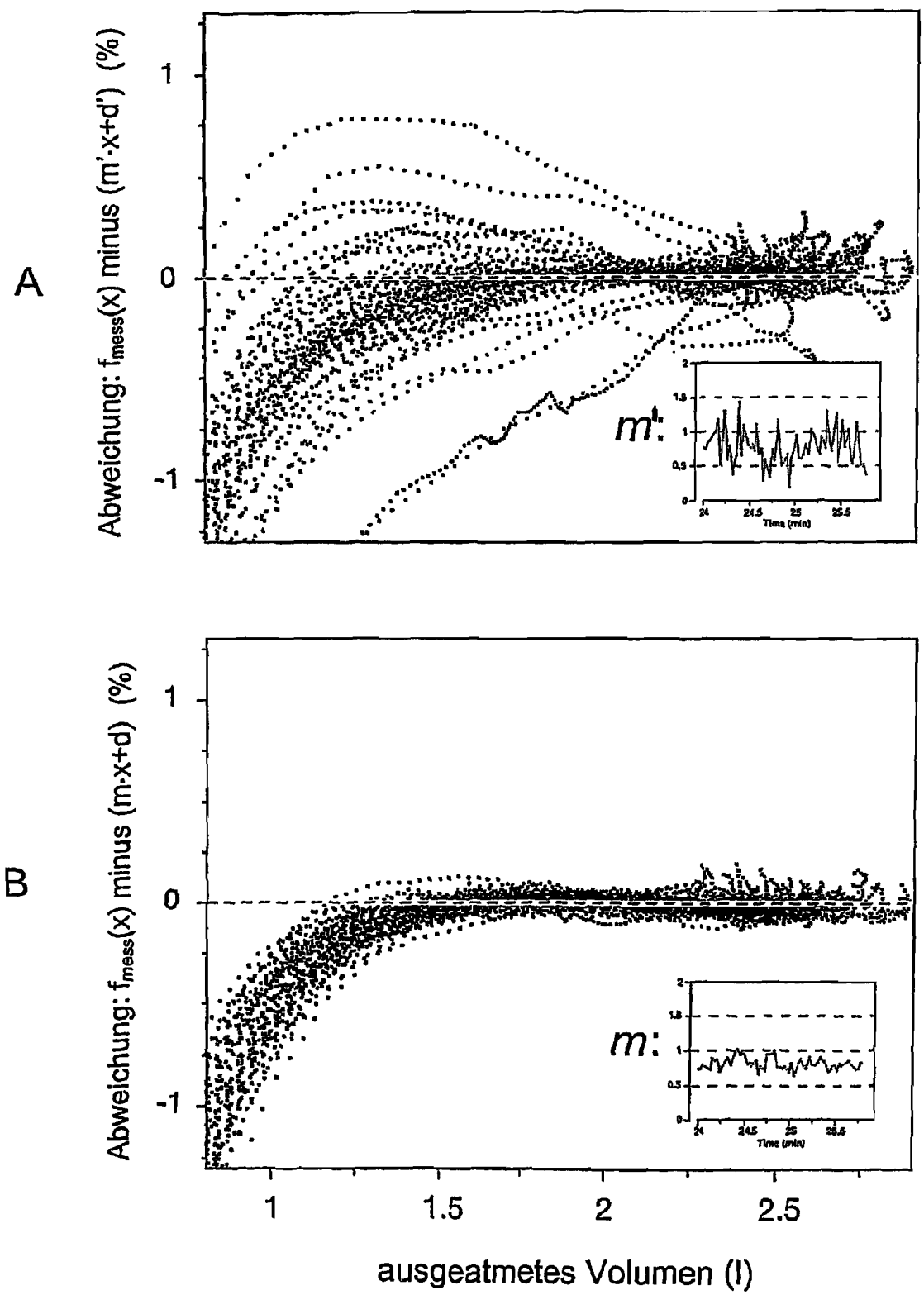
FIG. 10A shows percentage deviations between experimental expirogram data $f_{mess}$ and customary fit values.
FIG. 10B shows percentage deviations between experimental expirogram data $f_{mess}$ and customary fit values according to the present invention.

The improvement of the reliability, reproducibility and robustness of the interpretation of experimentally obtained expirograms based on an apparatus or method according to the present invention or one of its preferred embodiments compared to customary interpretation is illustrated in FIG. 10. It shows the percentage deviations between the measured values $f_{mess}(x_1), \ldots, f_{mess}(x_N)$ and the corresponding fitted values for the $CO_2$ expirograms of approximately 60 consecutive breaths. In particular, FIG. 10A shows the percentage deviations between the measured values $f_{mess}(x_1), \ldots, f_{mess}(x_N)$ and customary fit values $m'\cdot x_1+d', \ldots, m'\cdot x_N+d'$ as a function of the exhaled volume whereby for customary fit values only the linear ascending curve portion of the expirogram was fit with a straight line $m'\cdot x+d'$ with ascending gradient m'. By comparison FIG. 10A shows the deviations of the same experimental expirogram data $f_{mess}(x_1), \ldots, f_{mess}(x_N)$ of the values of the function $m\cdot x_1+d, \ldots, m\cdot x_1+d$ of a straight line $m\cdot x+d$ with an ascending gradient m, which corresponds to the linear portion $h(x)+Offest_{CO_2}$ of a fit function $f(x)=g(x)\cdot h(x)+Offset_{Gas}$ with $h(x)=m\cdot x+a$ according to a preferred embodiment of the present invention. In doing so a continuously differentiable, non-linear function g(x) in particular a function according to equation (5) with $$\lim_{x \to \infty} g(x) = 1 \text{ was used.}$$

While the data of the customary interpretation (FIG. 10A) scatter widely from breath to breath, they can be reproduced much better for the interpretation according to the invention (FIG. 10B). The comparison of the customary fit according to FIG. 10A and a fit according to the invention (FIG. 10B) thus shows that the deviation of the fit data between the experimental data and the deviation of the fit data of different breaths is clearly smaller. Thus the robustness and reproducibility of the interpretation of the expirograms can be markedly improved. This allows for a reliable assessment of the state of the lung that is examined.

REFERENCE NUMBER LIST 10 external air
12 respiratory tract
14 alveoli
16 capillaries
18 lung

The invention claimed is:

1. An apparatus for the acquisition and interpretation of expirograms comprising:
    a gas measuring probe configured to determine the gas concentration $f_{mess}$ of a gas in exhaled respiratory air;
    a reading device that is configured to read, for a plurality of values $x_1, \ldots, x_N$ of an exhaled volume of the exhaled respiratory air, the respective determined gas concentrations $f_{mess}(x_1), \ldots, f_{mess}(x_N)$ from the gas measuring probe;
    a storage device configured to store the values $x_1, \ldots, x_N$ assigned to the gas concentrations $f_{mess}(x_1), \ldots, f_{mess}(x_N)$; and
    a function fitting unit that is configured to determine a non-linear fit function $f(x)=g(x)\cdot h(x)+Offset_{Gas}$ for the stored gas concentrations $f_{mess}(x_1), \ldots, f_{mess}(x_N)$ by determining functions g(x) and h(x) wherein
    $h(x)=a+b\cdot x$
    g(x) is a continuously differentiable, non-linear function, where:

$$g(0) = 0 \text{ and } \lim_{x \to \infty} g(x) = const,$$

a, b and const are constants, and
    $Offset_{Gas}$ is a constant, mean concentration of the gas in room air.

2. The apparatus according to claim 1 further comprising an evaluation unit configured to determine the physiological dead space $x_{VD}$ of a respective lung, where $$\int_0^{x_{VD}} g(x)h(x)\,dx = \lim_{x_{max}\to\infty} \int_{x_{VD}}^{x_{max}} h(x)(1-g(x))\,dx$$

3. The apparatus according to claim 1, wherein g(x) is a monotonic function.

4. The apparatus according to claim 3 wherein $$g(x) = \cfrac{1}{1 + \cfrac{e^{(k_1 \cdot c - k_1 \cdot x)}}{1 + e^{\left(-\frac{2k_1 \cdot c k_2}{|k_1+k_2|} + \frac{2k_1 \cdot k_2 \cdot x}{|k_1+k_2|}\right)}} - \cfrac{e^{(k_2 \cdot c - k_2 \cdot x)}}{1 + e^{\left(-\frac{2k_1 \cdot c k_2}{|k_1+k_2|} + \frac{2k_1 \cdot k_2 \cdot x}{|k_1+k_2|}\right)}} + e^{(c \cdot k_2 - k_2 x)}} + k_3$$

where $k_1$, $k_2$, $k_3$ and c are constants.

5. The apparatus according to claim 1, wherein the function fitting unit is configured to determine the fit function $f(x)=g(x)h(x)+\text{Offset}_{Gas}$, according to the Marquardt-Levenberg algorithm.

6. The apparatus according to claim 1, wherein the storage unit is an electronic storage unit.

7. The apparatus according claim 1, further comprising an evaluation device configured to calculate the alveolar recruitment rate g'(x) by deriving the function g(x) based on the exhaled volume x.

8. The apparatus according to claim 7, further comprising a display device configured to display the alveolar recruitment rate g'(x) in a graphic manner.

9. A method for the acquisition and interpretation of expirograms, the method comprising:
measuring gas concentrations $f_{mess}(x_1), \ldots, f_{mess}(x_N)$ for a plurality of values $x_1, \ldots, x_N$ of an exhaled volume of exhaled respiratory air;
saving the measured gas concentrations; and
determining a non-linear fit function $$f(x)=g(x) \cdot h(x)+\text{Offset}_{Gas}$$

for the stored gas concentrations $f_{mess}(x_1), \ldots, f_{mess}(x_N)$ by determining functions g(x) and h(x) wherein:
$h(x)=a+b \cdot x$,
g(x) is a continuously differentiable, non-linear function, where:

$$g(0) = 0 \text{ and } \lim_{x\to\infty} g(x) = const,$$

a, b and const are constants, and
$\text{Offset}_{Gas}$ is a constant, mean concentration of the gas in room air.

10. The method according to claim 9 further comprising determining the physiological dead space $x_{VD}$ of a respective lung, wherein:

$$\int_0^{x_{VD}} g(x)h(x)\,dx = \lim_{x_{max}\to\infty} \int_{x_{VD}}^{x_{max}} h(x)(1-g(x))\,dx$$

11. The method according to claims 9, wherein:

$$g(x) = \cfrac{1}{1 + \cfrac{e^{(k_1 \cdot c - k_1 \cdot x)}}{1 + e^{\left(-\frac{2k_1 \cdot c k_2}{|k_1+k_2|} + \frac{2k_1 \cdot k_2 \cdot x}{|k_1+k_2|}\right)}} - \cfrac{e^{(k_2 \cdot c - k_2 \cdot x)}}{1 + e^{\left(-\frac{2k_1 \cdot c k_2}{|k_1+k_2|} + \frac{2k_1 \cdot k_2 \cdot x}{|k_1+k_2|}\right)}} + e^{(c \cdot k_2 - k_2 x)}} + k_3$$

where, $k_1$, $k_2$, $k_3$ and c are constants.

12. The method according to claim 9, wherein determining the fit function $f(x)=g(x)h(x)+\text{Offset}_{Gas}$, comprises determining the fit function according to the Marquardt-Levenberg algorithm.

13. The method according to claim 9, further comprising calculating the alveolar recruitment rate g'(x) by deriving the function g(x).

14. The method according to claim 13, further comprising graphically presenting the alveolar recruitment rate g'(x) on a display device.

15. A computer program product for interpreting expirograms that includes computer-executable instructions that, when executed by a computer processor, cause one or more processors to:
receive gas concentrations $f_{mess}(x_1), \ldots, f_{mess}(x_N)$ for a plurality of values $x_1, \ldots, x_N$ of an exhaled volume of exhaled respiratory air;
store the received gas concentrations; and
determine a non-linear fit function $$f(x)=g(x) \cdot h(x)+\text{Offset}_{Gas}$$

for the stored gas concentrations $f_{mess}(x_1), \ldots, f_{mess}(x_N)$ by determining functions g(x) and h(x)
wherein
$h(x)=a+b \cdot x$,
g(x) is a continuously differentiable, non-linear function with $$g(0) = 0 \text{ and } \lim_{x\to\infty} g(x) = const,$$

where
a, b and const are constants, and
$\text{Offset}_{Gas}$ is a constant, mean concentration of the gas in room air.

16. The computer program product according to claim 15, wherein the computer executable instructions further case one or more processors to determine the physiological dead space $x_{VD}$ of a respective lung wherein:

$$\int_0^{x_{VD}} g(x)h(x)\,dx = \lim_{x_{max}\to\infty} \int_{x_{VD}}^{x_{max}} h(x)(1-g(x))\,dx$$

17. The apparatus according to claim 2, wherein g(x) is a monotonic function, and wherein:

$$g(x) = \cfrac{1}{1 + \cfrac{e^{(k_1 \cdot c - k_1 \cdot x)}}{1 + e^{\left(-\frac{2k_1 \cdot c k_2}{|k_1+k_2|} + \frac{2k_1 \cdot k_2 \cdot x}{|k_1+k_2|}\right)}} - \cfrac{e^{(k_2 \cdot c - k_2 \cdot x)}}{1 + e^{\left(-\frac{2k_1 \cdot c k_2}{|k_1+k_2|} + \frac{2k_1 \cdot k_2 \cdot x}{|k_1+k_2|}\right)}} + e^{(c \cdot k_2 - k_2 x)}} + k_3,$$

and where $k_1$, $k_2$, $k_3$ and c are constants.

18. The apparatus according to claim 2, wherein the function fitting unit is configured to determine the fit function $f(x)=g(x) \cdot h(x)+\text{Offset}_{Gas}$ according to the Marquardt-Levenberg algorithm.

19. The method according to claim 10, wherein:

$$g(x) = \cfrac{1}{1 + \cfrac{e^{(k_1 \cdot c - k_1 \cdot x)}}{1 + e^{\left(-\frac{2k_1 \cdot c k_2}{|k_1+k_2|} + \frac{2k_1 \cdot k_2 \cdot x}{|k_1+k_2|}\right)}} - \cfrac{e^{(k_2 \cdot c - k_2 \cdot x)}}{1 + e^{\left(-\frac{2k_1 \cdot c k_2}{|k_1+k_2|} + \frac{2k_1 \cdot k_2 \cdot x}{|k_1+k_2|}\right)}} + e^{(c \cdot k_2 - k_2 x)}} + k_3,$$

where $k_1$, $k_2$, $k_3$, and c are constants.

20. The method according to claim 10, wherein determining the fit function $f(x)=g(x) \cdot h(x)+\text{Offset}_{Gas}$ comprises determining the fit function according to the Marqardt-Levenberg algorithm.

21. The apparatus according to claim 8, wherein the display device is configured to display the alveolar recruitment rate g' (x) in a graphic manner such that the alveolar recruitment rate g' (x) is graphically presented as a density of randomly distributed points.

22. The method according to claim 14, wherein the alveolar recruitment rate g' (x) is graphically presented on a display device such that the alveolar recruitment rate g' (x) is graphically presented as a density of randomly distributed points.

* * * * *

UNITED STATES PATENT AND TRADEMARK OFFICE
CERTIFICATE OF CORRECTION

PATENT NO.        : 7,885,771 B2
APPLICATION NO.   : 11/573631
DATED             : February 8, 2011
INVENTOR(S)       : Kai Roecker et al.

Page 1 of 3

It is certified that error appears in the above-identified patent and that said Letters Patent is hereby corrected as shown below:

On the title page, item (73), "Assignee", line 1, delete "Universitaetslinkum" and insert -- Universitaetsklinikum --, therefor.

In the Claims:

In column 16, line 55, in claim 1, after "wherein" insert -- : --.

In column 16, line 56, in claim 1, after "h(x)=a+b·x" insert -- , --.

In column 17, line 5-7, in claim 2, after " $\int_{0}^{x_{TD}} g(x)h(x)dx = \lim_{x_{max}\to\infty} \int_{x_{TD}}^{x_{max}} h(x)(1-g(x))dx$ " insert -- . --.

In column 17, line 12, in claim 4, delete "claim 3 wherein" and insert -- claim 3, wherein: --, therefor.

In column 17, line 23-24, in claim 5, delete "f(x)=g(x)h(x)+Offset$_{Gas}$," and insert -- f(x)=g(x)·h(x)+Offset$_{Gas}$ --, therefor.

In column 17, line 26, in claim 6, after "according" insert -- to --.

In column 17, line 28, in claim 7, after "according" insert -- to --.

In column 17, line 65, in claim 10, after " $\int_{0}^{x_{TD}} g(x)h(x)dx = \lim_{x_{max}\to\infty} \int_{x_{TD}}^{x_{max}} h(x)(1-g(x))dx$ " insert -- . --.

In column 18, line 1, in claim 11, delete "claims" and insert -- claim --, therefor.

Signed and Sealed this
Sixth Day of May, 2014

Michelle K. Lee
*Deputy Director of the United States Patent and Trademark Office*

CERTIFICATE OF CORRECTION (continued)
U.S. Pat. No. 7,885,771 B2

In column 18, line 10, in claim 11, delete "where," and insert -- where --, therefor.

In column 18, line 12, in claim 12, delete "f(x)=g(x)h(x)+Offset$_{Gas}$," and insert -- f(x)=g(x)·h(x)+Offset$_{Gas}$ --, therefor.

In column 18, line 34, in claim 15, after "wherein" insert -- : --.

In column 18, line 48, in claim 16, delete "case" and insert -- cause --, therefor.

In column 18, line 54-55, in claim 16, after "$\int_0^{x_{TP}} g(x)h(x)dx = \lim_{x_{max} \to \infty} \int_{x_{TP}}^{x_{max}} h(x)(1-g(x))dx$" insert -- . --.

In column 18, line 62-66, in claim 17, delete

"$g(x) = \dfrac{1}{1 + \dfrac{e^{(k_1 \cdot c - k_1 \cdot x)}}{1 + e^{\left(-\frac{2k_1 \cdot c \cdot k_2}{|k_1 + k_2|} + \frac{2k_1 \cdot k_2 \cdot x}{|k_1 + k_2|}\right)}} - \dfrac{e^{(k_2 \cdot c - k_2 \cdot x)}}{1 + e^{\left(-\frac{2k_1 \cdot c \cdot k_2}{|k_1 + k_2|} + \frac{2k_1 \cdot k_2 \cdot x}{|k_1 + k_2|}\right)}} + e^{(c \cdot k_2 - k_2 x)}} + k_3,$" and insert -- $g(x) = \dfrac{1}{1 + \dfrac{e^{(k_1 \cdot c - k_1 \cdot x)}}{1 + e^{\left(-\frac{2k_1 \cdot c \cdot k_2}{|k_1 + k_2|} + \frac{2k_1 \cdot k_2 \cdot x}{|k_1 + k_2|}\right)}} - \dfrac{e^{(k_2 \cdot c - k_2 \cdot x)}}{1 + e^{\left(-\frac{2k_1 \cdot c \cdot k_2}{|k_1 + k_2|} + \frac{2k_1 \cdot k_2 \cdot x}{|k_1 + k_2|}\right)}} + e^{(c \cdot k_2 - k_2 x)}} + k_3,$ --, therefor.

In column 19, line 9-14, in claim 19, delete

"$g(x) = \dfrac{1}{1 + \dfrac{e^{(k_1 \cdot c - k_1 \cdot x)}}{1 + e^{\left(-\frac{2k_1 \cdot c \cdot k_2}{|k_1 + k_2|} + \frac{2k_1 \cdot k_2 \cdot x}{|k_1 + k_2|}\right)}} - \dfrac{e^{(k_2 \cdot c - k_2 \cdot x)}}{1 + e^{\left(-\frac{2k_1 \cdot c \cdot k_2}{|k_1 + k_2|} + \frac{2k_1 \cdot k_2 \cdot x}{|k_1 + k_2|}\right)}} + e^{(c \cdot k_2 - k_2 x)}} + k_3,$" and insert -- $g(x) = \dfrac{1}{1 + \dfrac{e^{(k_1 \cdot c - k_1 \cdot x)}}{1 + e^{\left(-\frac{2k_1 \cdot c \cdot k_2}{|k_1 + k_2|} + \frac{2k_1 \cdot k_2 \cdot x}{|k_1 + k_2|}\right)}} - \dfrac{e^{(k_2 \cdot c - k_2 \cdot x)}}{1 + e^{\left(-\frac{2k_1 \cdot c \cdot k_2}{|k_1 + k_2|} + \frac{2k_1 \cdot k_2 \cdot x}{|k_1 + k_2|}\right)}} + e^{(c \cdot k_2 - k_2 x)}} + k_3,$ --, therefor.

In column 20, line 3, in claim 20, delete "Marqardt-Levenberg" and insert -- Marquardt-Levenberg --, therefor.

In column 20, line 7-8, in claim 21, delete "g' (x)" and insert -- g'(x) --, therefor.

CERTIFICATE OF CORRECTION (continued)
U.S. Pat. No. 7,885,771 B2

In column 20, line 9, in claim 21, delete "g' (x)" and insert -- g'(x) --, therefor.

In column 20, line 12, in claim 22, delete "g' (x)" and insert -- g'(x) --, therefor.

In column 20, line 13, in claim 22, delete "g' (x)" and insert -- g'(x) --, therefor.